United States Patent
Rosenblatt et al.

(10) Patent No.: US 9,066,910 B2
(45) Date of Patent: Jun. 30, 2015

(54) METHODS AND COMPOSITIONS OF CANNABIS EXTRACTS

(76) Inventors: Steven Rosenblatt, Los Angeles, CA (US); Jeffrey Tucker, Los Angeles, CA (US); Steve DeAngelo, Los Angeles, CA (US)

( * ) Notice: Subject to any disclaimer, the term of this patent is extended or adjusted under 35 U.S.C. 154(b) by 717 days.

(21) Appl. No.: 12/760,932

(22) Filed: Apr. 15, 2010

(65) Prior Publication Data

US 2011/0256245 A1    Oct. 20, 2011

(51) Int. Cl.
*A61K 36/00*     (2006.01)
*A61K 36/185*    (2006.01)

(52) U.S. Cl.
CPC ......... *A61K 36/185* (2013.01); *A61K 2236/331* (2013.01)

(58) Field of Classification Search
None
See application file for complete search history.

(56) References Cited

U.S. PATENT DOCUMENTS 6,158,591 A * 12/2000 Delp ............................... 209/17

OTHER PUBLICATIONS

Website document entitled: "How to make wicked Hash" (available at http://www.cannabisculture.com/content/how-make-wicked-hash) Downloaded from websited Aug. 15, 2012.*
Ben Amar (2006) Journal of Ethnopharmacology 105: pp. 1-25.*
Conti et al. (2002) Brit. J. Pharm. 135, pp. 181-187.*
Croci et al. (2007) Brit. J. Pharm. 150, pp. 559-566.*
Richardson (2000) The Journal of Pain, vol. 1, No. 1, pp. 2-14.*
Tramer et al. (2001) Brit. Med. Journal. vol. 323, pp. 1-8.*
Website document entitled: "Bubble Hash & THC Extraction" (Available at http://informationon.com/bubble-has-hashish) Downloaded from website Aug. 15, 2012.*
Website document entitled: "Home-made hash" (available at http://www.cannibisculture.com/articles/4117.html) Dated to Mar. 8, 2005.*
Website document entitled: "Making Ice-Water with Matt Rize" (available at http://medicalmarijuana.com/how-to-make-hash-ice-water). Dated to May 31, 2011.*
Website document entitled: "Ice-water separation" (available at http://en.wikipedia.org/wiki/ice-water_separation). Dated to Sep. 13, 2006.*

* cited by examiner

*Primary Examiner* — Chris R Tate
*Assistant Examiner* — Russell Fiebig
(74) *Attorney, Agent, or Firm* — Partners Law Group, Inc.; Steve Hassid; Chen Huang

(57) ABSTRACT

In one embodiment, a method is provided for obtaining an extract from a cannabis plant for medical uses. In one embodiment, a method for obtaining an extract from a cannabis plant for medical uses is provided. The method comprises (a) providing cannabis flower trimmings with trichome material, (b) providing clean, cold water to at least cover cannabis the cannabis flower trimmings, (c) agitating the mixture of cannabis flower trimmings and water (d) soaking the cannabis flower trimming in cold water for at least one minute, (e) removing cannabis flower trimmings from the water, (f) removing the trichome material from the water and (g) drying the trichome material to contain no more than 10% total water weight.

2 Claims, 10 Drawing Sheets

METHODS AND COMPOSITIONS OF CANNABIS EXTRACTS

BACKGROUND

1. Field

This disclosure relates generally to extracts used for medical purposes and more specifically to cannabis-related products and extracts that provide various benefits and advantages to a mammal.

2. General Background

Cannabis products have been consumed in various forms for thousands of years. The first descriptions of the medical uses date from Chinese herbal texts in the first century A.D. Cannabis products were taken orally in an herbal tea concoction and were used for their pain-relieving and sleep-inducing properties.

In contrast, the use of cannabis in India was largely restricted to smoking the leaf or the resin extract (hashish) for its psychoactive properties. In fact, cannabis was also used in Ayurvedic medicine in India. This practice became incorporated into the Indian life and culture.

The use was spread through Arab lands in the Middle Ages before coming into Europe and the Americas. It was either eaten, usually in the hashish form, or the leaves were smoked. The medical benefits were not utilized by the medical practitioners of the time and the major usage was for its psychoactive properties as a recreational drug.

It was not until the middle of the nineteenth century that cannabis-based medicines were introduced into the West. The tinctures were used orally for the treatment of seizures, neuralgia, insomnia, and dysmenorrhea, among other illnesses. The cannabis-based medications were administered through an alcohol-based extract of hemp plants that were lacking in the most pharmacologically active ingredients, especially tetrahydrocannabinol (THC).

During most of the twentieth century there has been little interest in or advance of the medical use of cannabis. It has been legally prohibited in the United States since 1937. Occasionally small amounts of oil extract have been made available to some licensed university researchers for animal studies. One of the current authors (Stephen Rosenblatt, M.D., Ph.D.) did animal research from 1969 through 1971 on learning and memory in rats, using injectable THC oil. Little to no human research on the medical uses of cannabis has been done in recent years. It is believed that, to the extent not already legalized, full state and federal legalization of cannabis related products is imminent.

There presently exists the need to provide more effective and safer cannabis extracts for various medical uses, extraction methods that provide unique active compounds that are useful to treat pain and various medical conditions. Additionally, presently known extraction procedures add unwanted toxins and solvents, provide relatively low yields of the active compound, and/or do not provide the desired active ingredient(s) for the particular pain related to medical purpose. The present invention overcomes these limitations and provides other related advantages.

SUMMARY

In one embodiment of the present disclosure, a method for obtaining an extract from a cannabis plant for medical uses is provided. The method comprises (a) providing cannabis flower trimmings with trichome material, (b) providing clean, cold water to at least cover cannabis the cannabis flower trimmings, (c) agitating the mixture of cannabis flower trimmings and water (d) soaking the cannabis flower trimming in cold water for at least one minute, (e) removing cannabis flower trimmings from the water, (f) removing the trichome material from the water and (g) drying the trichome material to contain no more than 10% total water weight.

In another embodiment of the present disclosure, a whole plant extract of cannabis is produced by a whole plan extract is provided by solvent extractions of raw cannabis flowers. It should be appreciated that the present disclosure includes any other known methods of producing a whole plant extract of cannabis, parts of which may be incorporated into the present disclosure.

In at least one aspect of at least one embodiment of the present disclosure, the method further includes heating the dried trichome material to at least 150 degrees Fahrenheit for at least 15 minutes.

In at least one aspect of at least one embodiment of the present disclosure, the method further includes heating the whole plant extract to at least 150 degrees Fahrenheit for at least 15 minutes.

In another aspect of at least one embodiment of the present disclosure, the method further includes pulverizing or grinding up the trichome material into small particles, adding a water soluble organic compound to the ground up or pulverized sieved cannabis flower trimmings to create a paste, adding a cream to the paste until the paste is a smooth ointment, and processing the ointment through an ointment mill until the ointment is evenly colored.

In yet another aspect of at least one embodiment, the whole plant extract is mixed with a water-soluble organic compound to create a paste and then added to a cream to the paste until the paste is a smooth ointment.

In yet another aspect of at least one embodiment, the ointment is processed through an ointment mill.

In yet another aspect of at least one embodiment of the present disclosure, the method further includes adding the dried sieved cannabis flower trimmings to a lipophilic compound or equivalent carrying agent.

In yet another aspect of at least one embodiment of the present disclosure, the method further includes adding the whole plant extract to a lipophilic compound or equivalent carrying agent.

In yet another aspect of at least one embodiment of the present disclosure, the method further includes providing the extract to a mammal to treat arthritis in a mammal.

In yet another aspect of at least one embodiment of the present disclosure, the method further includes providing the ointment to a mammal to treat arthritis in a mammal.

In yet another aspect of at least one embodiment of the present disclosure, the method further includes providing the extract to a mammal to treat pain in a mammal.

In yet another aspect of at least one embodiment of the present disclosure, the method further includes providing the ointment to a mammal to treat pain in a mammal.

In yet another aspect of at least one embodiment of the present disclosure, the method further includes providing the extract to a mammal to treat tendonitis in a mammal.

In yet another aspect of at least one embodiment of the present disclosure, the method further includes providing the ointment to a mammal to treat tendonitis in a mammal.

In yet another aspect of at least one embodiment of the present disclosure, the method further includes providing the extract to a mammal to treat inflammation in a mammal.

In yet another aspect of at least one embodiment of the present disclosure, the method further includes providing the ointment to a mammal to treat inflammation in a mammal.

In yet another aspect of at least one embodiment of the present disclosure, the method further includes providing the extract to a mammal to treat vomiting in a mammal.

In yet another aspect of at least one embodiment of the present disclosure, the method further includes providing the ointment to a mammal to treat vomiting in a mammal.

In another embodiment of the present disclosure, a method is provided for reducing the effects of nausea or vomiting in a mammal. The method comprises providing an ointment containing a cold-press extract of cannabis flower trimmings, where the extract was obtained by combining cannabis flower trimmings with enough cold water and ice to cover the cannabis flower trimmings, agitating the mixture of cannabis flower trimmings, soaking them in water and ice for at least two minutes, removing the water and ice through one or more mesh screens, drying the sieved cannabis flower trimmings for at least one week, grinding the dried cannabis flower trimmings and adding the ground up dried cannabis flower trimmings to a carrier or lipophilic compound to create an ointment.

In another aspect of at least one embodiment, the ointment can contain a whole plant cannabis extract, water-soluble organic compound, and/or a lipophilic compound or equivalent carrying agent.

In yet another embodiment of the present disclosure, a method of reducing the effects of nausea or vomiting in a mammal is provided. The method comprises providing the mammal with an ointment containing a cold press extract of cannabis flower trimmings wherein the extract was obtained by combining cannabis flower trimmings with enough cold water and ice to cover the cannabis flower trimmings, agitating the mixture of cannabis flower trimmings, soaking the cannabis flower trimmings in cold water for at least one minute, grinding the dried cannabis flower trimming and adding the ground up dried cannabis flower trimmings to a lipophilic compound to create an ointment containing the ground up dried cannabis flower trimmings.

In yet another aspect of at least one embodiment of the present disclosure, the method further includes claiming that the ointment reduces the effects of nausea or vomiting in the mammal.

In yet another embodiment of the present disclosure, a method is provided for reducing pain in a mammal. The method comprises providing a composition containing an effective amount of delta-9-tetrahydrocannabinol acid to a mammal and claiming that the composition reduces pain in the mammal.

In yet another aspect of at least one embodiment of the present disclosure, the method further includes providing the extract to a mammal to treat psoriasis in a mammal.

In yet another aspect of at least one embodiment of the present disclosure, the method further includes claiming that the composition does not create psychedelic effects associated with tetrahydrocannabinol.

In yet another aspect of at least one embodiment of the present disclosure, the composition is provided as a topical ointment or gel.

In yet another aspect of at least one embodiment of the present disclosure, the composition further contains a lipophilic compound.

In yet another aspect of at least one embodiment of the present disclosure, the composition further contains a lipophilic compound which acts as a carrier agent for the composition and penetrates the skin of the mammal.

In yet another aspect of at least one embodiment of the present disclosure, the composition further contains glycerin.

In yet another aspect of at least one embodiment of the present disclosure, the composition further contains a lipophilic cream.

In yet another aspect of at least one embodiment of the present disclosure, the composition further contains a water-soluble organic compound.

In yet another aspect of at least one embodiment of the present disclosure, the composition primarily affects or binds to the CB2 receptor sites and CB1 pns receptors of the mammal.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Figure 1:
FIG. 1 shows the back of a patient with psoriasis lesions before treatment with a cannabis extract.

In one embodiment of the present disclosure, the extraction procedure and delivery approach are provided that allow selective utilization of various cannabinoid molecules from the whole cannabis sativa plant. These various cannabinoid compounds are designed to selectively affect various cannabinoid receptors in the nervous system, immune system and other tissues. In one aspect of at least one embodiment of the present disclosure, the extract is an oil-based whole plant product that contains all of the active compounds contained in the cannabis plant. In one embodiment of the present disclosure, the methods of obtaining the active compounds are explained in the "Procedure Methodology" section referenced below. In another aspect of at least one embodiment of the present disclosure, the whole cannabis plant product is then allowed to dry after one of the extraction methods described herein is performed. In yet another aspect of at least one embodiment of the present disclosure, one portion of the whole cannabis plant product is then heated while the other segment is left at room temperature. In yet another aspect of at least one embodiment, the heat-formulated (CEh) cannabis extract is kept separated from the cold-formulated (CEc) cannabis extract.

In another embodiment of the present disclosure, a method for obtaining an extract from a cannabis plant for medical uses is provided. The method comprises (a) providing cannabis flower trimmings with trichome material, (b) providing clean, cold water to at least cover cannabis the cannabis flower trimmings, (c) agitating the mixture of cannabis flower trimmings and water (d) soaking the cannabis flower trimming in cold water for at least one minute, (e) removing cannabis flower trimmings from the water, (f) removing the trichome material from the water and (g) drying the trichome material to contain no more than 10% total water weight.

It should be appreciated that each of the methods of extraction disclosed herein provide an extract with specific physiological properties that are mediated through separate pathways and receptors, which provide numerous benefits and advantages, as discussed herein.

Cannabinoid Receptor Mechanisms

Mammalian tissues contain two types of cannabinoid receptors that have been identified, CB1 and CB2. CB1 receptors are expressed mainly by neurons of the central and peripheral nervous system (CB1cns and CB1pns). CB2 receptors are located on non-neuronal tissues, particularly on immune cells throughout the body.

The psychoactive effect of cannabis is mediated by selective stimulation of the CB1cns receptors. This action is produced by agonistic actions on these G protein coupled receptor sites in the central nervous system. The major active ingredient in the cannabis extract that acts agonistically on the CB1cns receptors is delta-9-tetrahydrocannabinol (THC).

The CB1 pns receptors have a greater effect on pain modulation. When stimulated agonistically they act to produce anti-nociception in animal models of acute pain. Additionally the stimulation of these receptor sites in animals has been shown to suppress signs of tonic pain induced by nerve damage or the injection of an inflammatory agent.

The CB2 receptors are located on immune cells of the body and as such when stimulated act to inhibit, evoke immune cell migration and modulate cytokine release. The action on these receptors may act to produce an anti-nociception effect through the suppression of inflammatory mediators. Additionally there appear to be other effects on the immune system through stimulation of the CB2 receptors.

The action on the CB2 receptors is effected by one of the non-psychoactive cannabinoid extracts from the whole plant. This main non-psychoactive compound is delta-9-tetrahydrocannabinol acid (THCa) that acts to affect the immune system through its ability to inhibit tumor necrosis factor alpha (TCF-alpha).

THCa has also been found to have a partial agonistic effect on the CB1 pns receptors, which act to modulate peripheral pain reception. This direct action of THCa on these receptors in the peripheral nervous system also has an anti-nociception effect as demonstrated in animal studies.

The Cannabis Sativa Extract In yet another embodiment of the present invention, the extract of Cannabis is divided into two distinct forms:

(1) The unheated total plant extract of Cannabis (CEc) is extracted at a very low temperature and is composed of a chief ingredient of THCa. CEc has specialized properties and affects on receptors, thus providing unique medicinal properties. Several preliminary studies, the results of which applicants intend to include in other patents, have shown this unheated total plant extract to be affective in treating a variety of medical conditions.

(2) The heat-treated Cannabis extract (CEh) has a chief active ingredient of THC and selectively stimulates the CBcns receptor sites located in the brain.

In yet another embodiment of the present invention, a Cannabis extract is provided which is heat-treated. The heat-treated Cannabis extract (CEh) contains as a major ingredient a decarboxylated form of the molecule THC. This has a major affect on the CB1 receptors located in the central nervous system.

The Cannabis extract that is cold-treated has more affinity for the CB2 receptors. Its action is focused on the peripheral receptors that modulate pain and inflammation.

In yet another embodiment of the present disclosure, a method of reducing the effects of nausea or vomiting in a mammal is provided. The method comprises providing the mammal with an ointment containing a cold press extract of cannabis flower trimmings wherein the extract was obtained by combining cannabis flower trimmings with enough cold water and ice to cover the cannabis flower trimmings, agitating the mixture of cannabis flower trimmings, soaking the cannabis flower trimmings in cold water for at least one minute, grinding the dried cannabis flower trimming and adding the ground up dried cannabis flower trimmings to a lipophilic compound to create an ointment containing the ground up dried cannabis flower trimmings.

In yet another embodiment of the present invention, the methods and compounds of the present invention can be applied topically, which eliminates the need for smoking or otherwise inhaling the extracts, which causes damage to the lungs (often caused by inhaling the burning plant material). Additionally, it does not need to be taken orally and go through the digestive system and the liver, which will alter the biochemistry of the extract. It is absorbed into the skin and directly into the blood stream to have both local and distal effects.

In yet another embodiment, the extracted Cannabis plant compounds are applied by a topical application using a penetrating lipophilic compound as a carrier agent. This represents an original advancement in the construction of a unique biochemical agent for the treatment of a multitude of diseases in several diverse organ systems.

The Cannabis Extract: Procedural Methodology

In yet another embodiment of the present disclosure, a method is provided for providing a cannabis extract. The method comprises the following ingredients and methodology.

Ingredients:
600 grams of trimmings from cannabis flowers (trimmings consist mostly of small leaf material);
20 gallons of clean water;
12 pounds of ice.

General Steps (Can be performed in different order than listed):
1. Place 600 grams of cannabis flower trimmings in large vat;
2. Add 20 gallons of clean, cold water;

3. Add 12 pounds of ice;
4. Agitate vigorously;
5. Filter water through a series of five mesh screens, of progressively smaller mesh;
6. Discard plant material that collects on top screen;
7. Remove trichome material from each of the four remaining mesh screens, one by one. Do not mix;
8. Place material in 12-inch square fine mesh hand cloth. Twist vigorously to remove as much water as possible. Discard water that is squeezed out;
9. One by one, place material from the four mesh screens, into fine mesh stainless steel sieves. Press material through sieves, onto plates or a glass topped table;
10. Spread sieved material as thinly as possible on plate or glass surface. Keep each batch of material separate from the others. Do not mix;
11. Place plates of material in a cool, dry, dark environment, and allow to dry and cure for at least two weeks;
12. Grade material into high and low purity sections;
13. Once thoroughly dried (material should lose approximately ⅔ of its weight as water evaporates), high purity material is ready for use.

At least a portion of the dried material is separated and is prepared for heat treatment and can be referred to as heat-treated extract (CEh):

This portion is then heated in special drying ovens at a temperature of 248 degrees Fahrenheit for 60 minutes.

Topical Preparation:
1. Weigh dry ingredients.
2. Place powder into a glass mortar and pulverize into small particles with pestle.
3. Slowly add glycerin and stir into powder until a thick paste is formed.
4. Geometrically add liposomal cream into the active ingredient and stir until smooth.
5. Run this cream through an ointment mill on setting #3 one time, then on setting #2 two times, then on setting #1 two times until completely smooth and evenly colored.
6. Package into desired container and label.

Clinical Application of the Cannabis Extract

Preliminary research has shown the actions of the Cannabis extract to have wide-ranging beneficial effects on a number of medical conditions. Clinical research has been focused on four areas of medical problems which seem to show a beneficial effect from either the CEc or the CEh forms:

(1) Chronic pain has been shown by several studies to be controlled by use of Cannabis. Our use of a topical application of CEc in dermal penetrating cream has been effective in relieving chronic pain conditions of arthritis and tendonitis. The use of a topical application of the extract in a penetrating cream formulation allows the medication to directly affect the local receptor sites. This direct application at the affected sites allows rapid modulation of the pain and inflammation of these chronic conditions.

A specific pain condition that has been effectively treated by the use of CEc is fibromyalgia. This chronic debilitating condition involves local pain at specific sites on the body. The use of this extract allows stimulation of the CB2 receptor sites in the local pain areas as well as stimulation of the CB1pns receptors. This disease, which is a combination of autoimmune and inflammatory conditions, responds extremely well to topical applications of the CEc.

(2) The autoimmune diseases seem to respond very well to the application of CEc. This is because of the action on the CB2 receptors which are located on several different cells lines in the immune system. Through the inhibition of TCF-alpha Cannabis has a beneficial effect on patients with multiple sclerosis and lupus. These severe and chronic autoimmune diseases have been shown in several studies to respond to smoked Cannabis. Our preliminary studies have shown the topical application to be effective without the psychoactive side effects. By selective stimulation of the CB2 receptors the immune modulation effects of the CEc have a beneficial effect on multiple sclerosis and lupus without the central nervous system effects.

(3) Nausea and vomiting that are unresponsive to other medications have been shown to be helped through the use of Cannabis. The use of CEc has a modulating effect on nausea and vomiting without the psychoactive properties that smoking the Cannabis plant can cause in a mammal. This has been shown to be especially useful in helping with the side effects of chemotherapy. Additionally animal studies show an increase in hunger and feeding behavior through the action of the CB2 receptors in animal studies.

Figure 2:
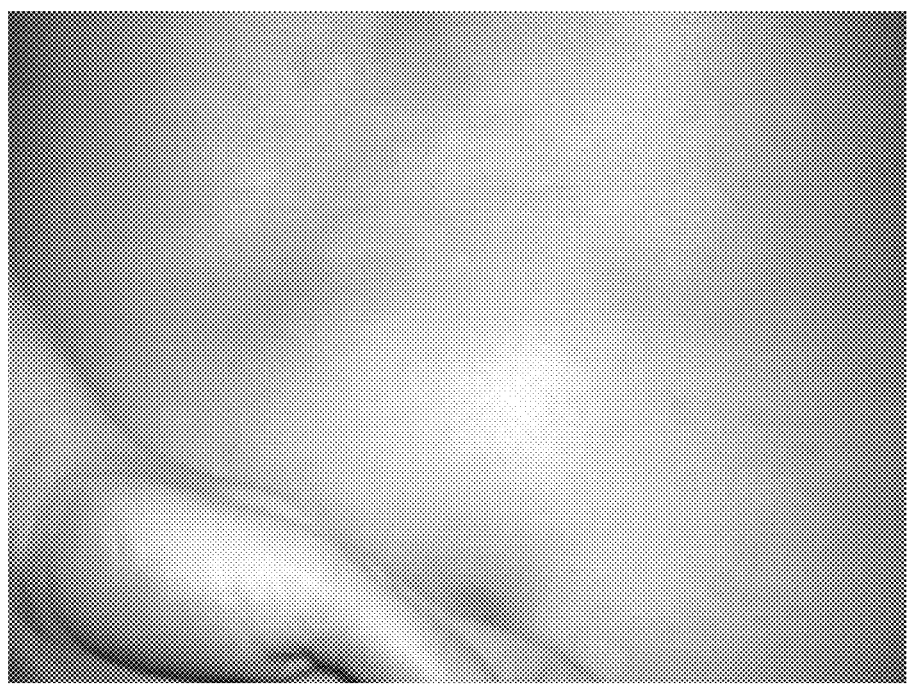
FIG. 2 shows the back of a patient with psoriasis lesions after treatment with a cannabis extract.
Figure 3:
FIG. 3 shows a right-side view of a patient with psoriasis lesions after treatment with a cannabis extract.
Figure 4:
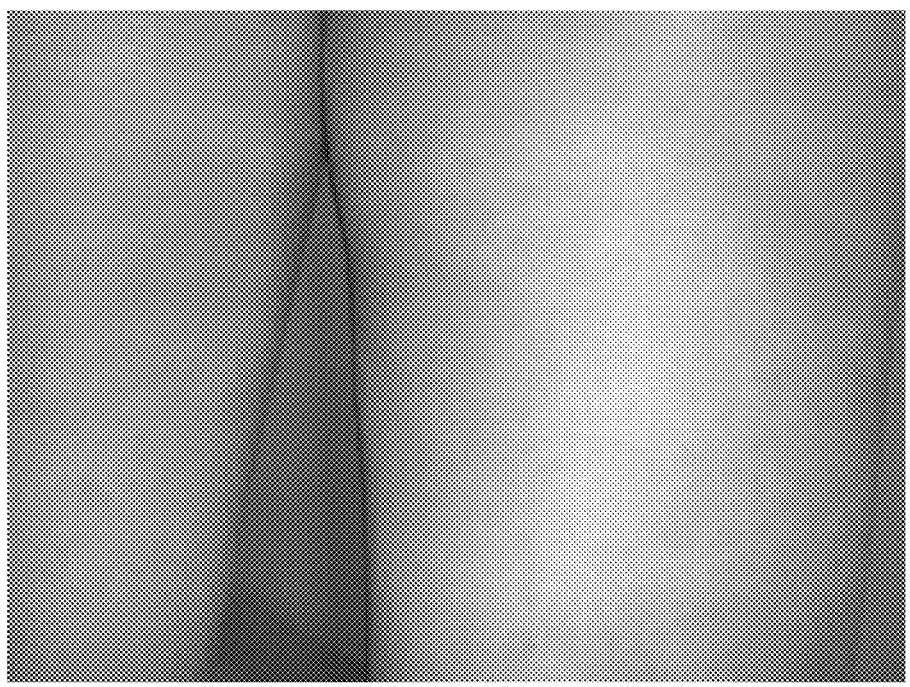
FIG. 4 shows the back of the legs of a patient with psoriasis lesions before treatment with a cannabis extract.
Figure 5:
FIG. 5 shows the back of the legs of a patient with psoriasis lesions after treatment with a cannabis extract.
Figure 6:
FIG. 6 shows the left palm of a patient with psoriasis lesions before treatment with a cannabis extract.
Figure 7:
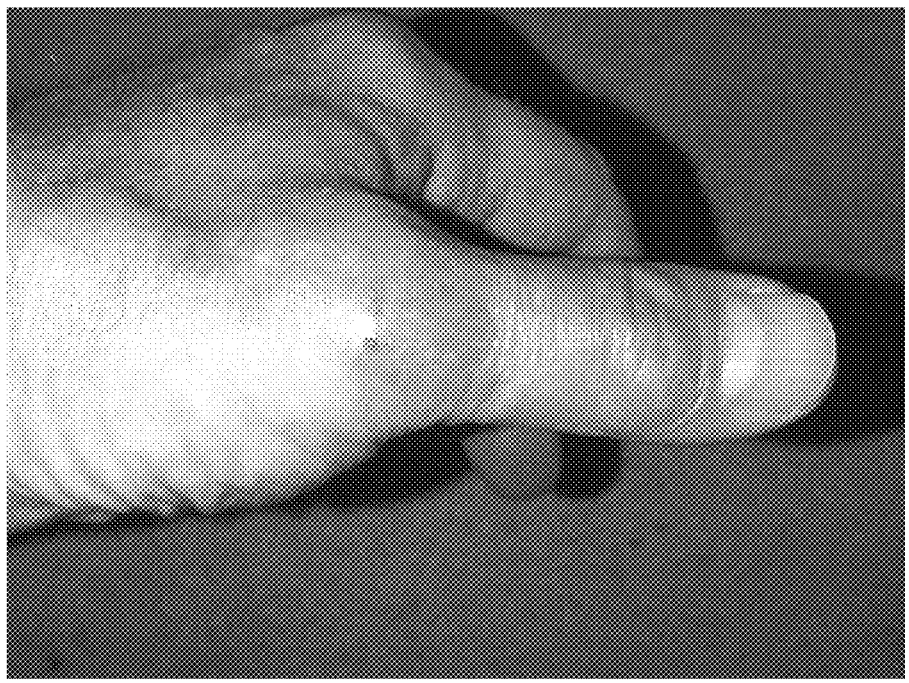
FIG. 7 shows the left thumb of a patient with psoriasis lesions after treatment with a cannabis extract.
Figure 8:
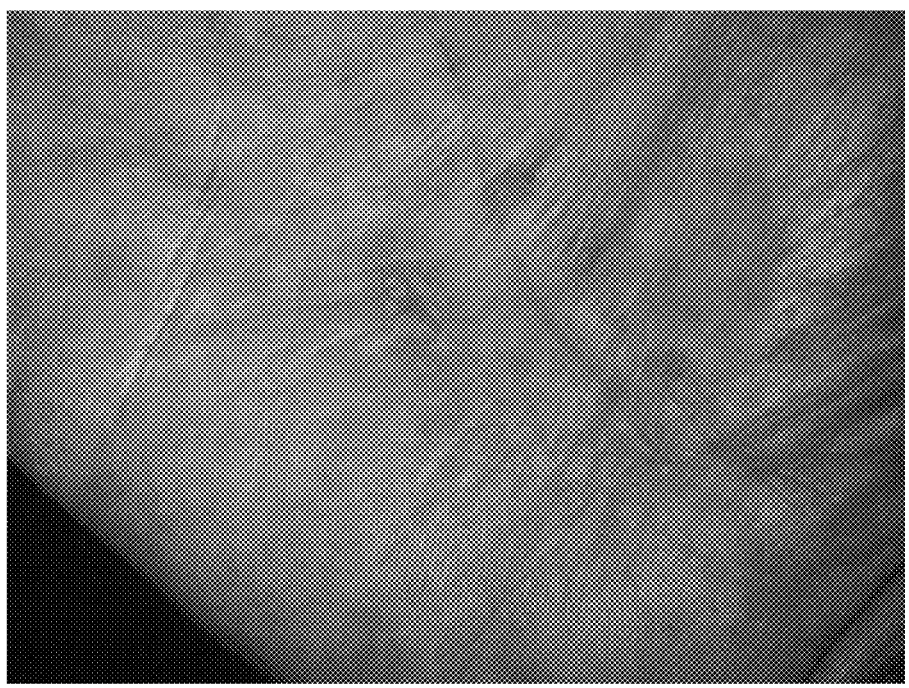
FIG. 8 shows the right palm of a patient with psoriasis lesions after treatment with a cannabis extract.
Figure 9:
FIG. 9 shows the left palm of a patient with psoriasis lesions during treatment with a cannabis extract.
Figure 10:
FIG. 10 shows the left thumb of a patient with psoriasis lesions during treatment with a cannabis extract.
Figure 11:
FIG. 11 shows the right palm of a patient with psoriasis lesions during treatment with a cannabis extract.
Figure 12:
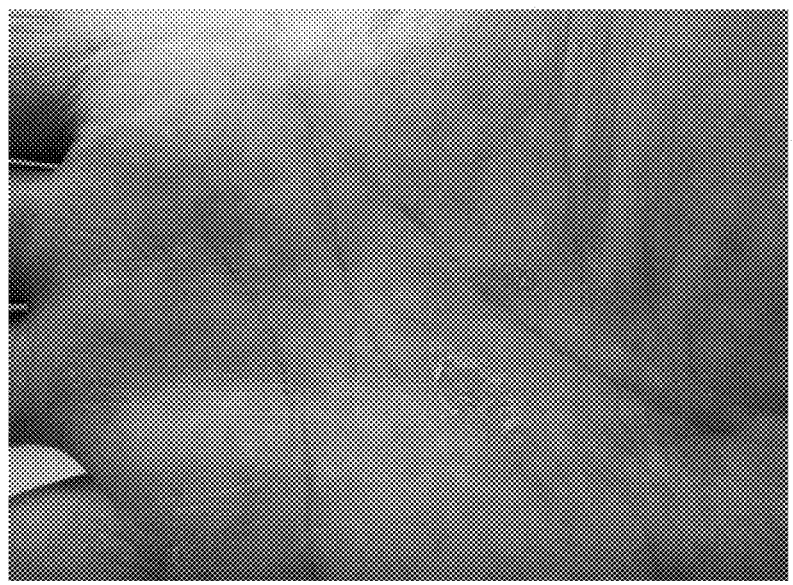
FIG. 12 shows the right palm of a patient with psoriasis lesions during treatment with a cannabis extract.
Figure 13:
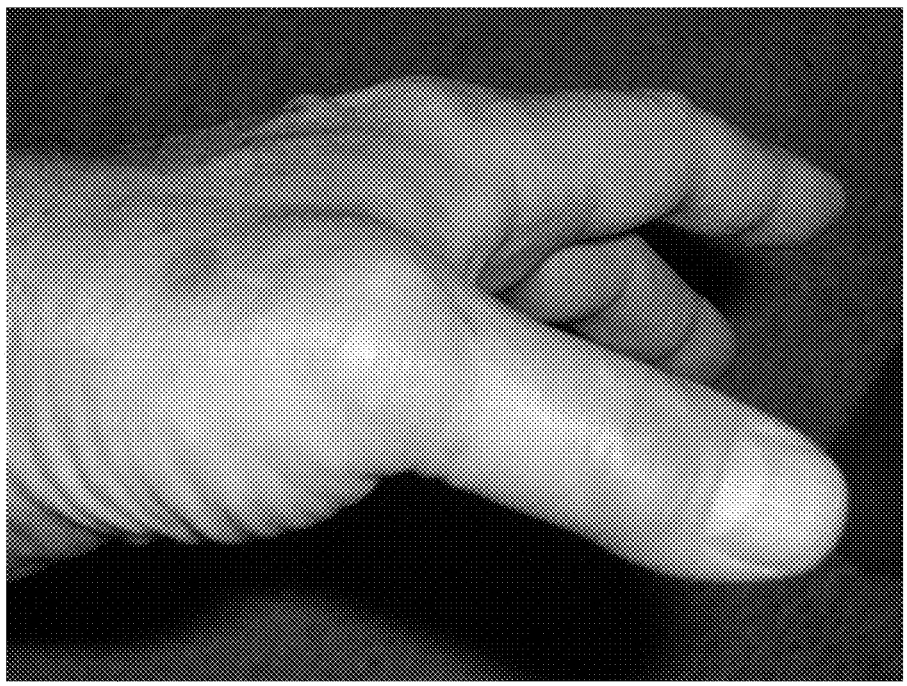
FIG. 13 shows the right palm of a patient with psoriasis lesions after treatment with a cannabis extract.
Figure 14:
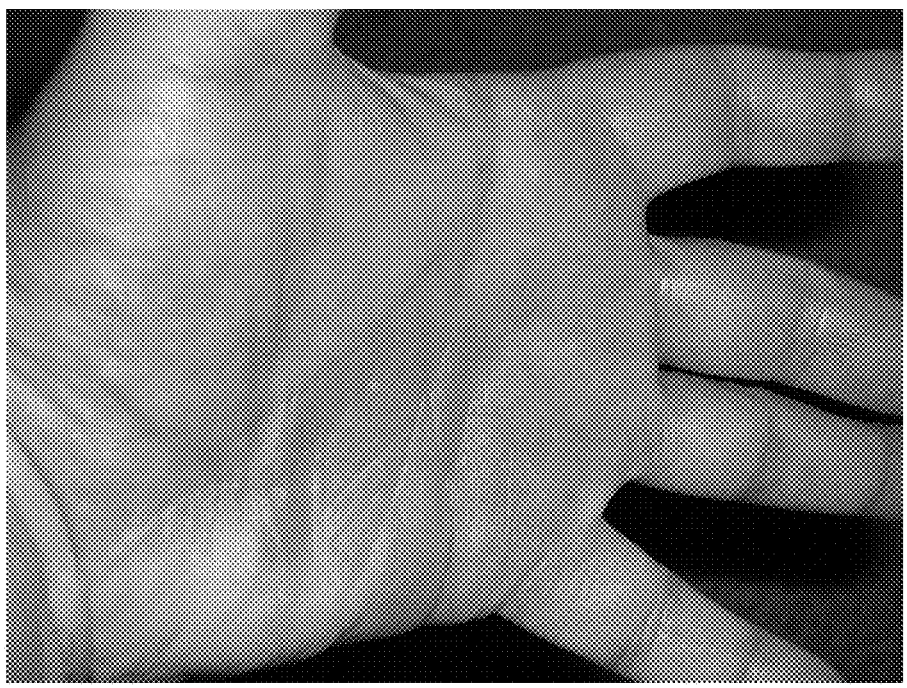
FIG. 14 shows the left thumb of a patient with psoriasis lesions after treatment with a cannabis extract.
Figure 15:
FIG. 15 shows the right palm of a patient with psoriasis lesions after treatment with a cannabis extract.
Figure 16:
FIG. 16 shows the right palm of a patient with psoriasis lesions after treatment with a cannabis extract.
Figure 17:
FIG. 17 shows the left palm of a patient with psoriasis lesions after treatment with a cannabis extract.
Figure 18:
FIG. 18 shows the left thumb of a patient with psoriasis lesions after treatment with a cannabis extract.
Figure 19:
FIG. 19 shows the right palm of a patient with psoriasis lesions after treatment with a cannabis extract.

As shown from the results of FIGS. 1-19, the application of the topical cannabis extract, as described and claimed herein, has been shown to have a positive effect on the healing of psoriasis lesions. A pilot study was conducted using five patients (2 males and 3 females) who had active psoriatic lesions on various body surfaces. Patients were known patients of Dr. Steven Rosenblatt and had been followed for several months before the beginning of the study to obtain a baseline measure of the extent of the skin lesions.

The material used in the study was a water-extracted cannabis product that was formulated with a penetrating gel for topical application. It was formulated in a strength of 100 mg extract per 1 ml of gel. This was supplied in a precision topical dispenser designed to disperse a set amount of product for each application.

Patients were instructed to apply a small amount (0.5 ml) to each lesion or cluster of lesions two times per day. They were instructed to rub the cream into the lesions until it was fully absorbed.

Patients were asked to rate the severity and extent of the lesions in a 0 to 5 scale, with 5 being the worse and 0 being no lesion visible. Rating was done weekly beginning with the date of the first application.

Results showed all subjects had reduced lesion severity and extent based on the rating scale. The average of the subjects at the beginning of the study was 3.75 and after two weeks of topical application they averaged 2.75. This rating then dropped to 2.00 after the fourth week.

One patient dramatically improved from 4.0 with extensive lesions to 1.0 after four weeks of application. All patients in the study showed dramatic improvement and enthusiastically wished to continue the treatment.

FIGS. 1-19 demonstrate the effects of the cannabis extract on psoriasis lesions.

It should be appreciated that the present disclosure includes use of any known alternative method of producing a whole plant extract of cannabis to provide the methods of the present application.

While the compositions and methods of the present disclosure have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:
1. A method for producing a topical ointment composition comprising an effective amount of high-purity trichomes from cannabis flower trimmings, the method comprising:
   a. adding cannabis flower trimmings to ice water to at least cover the cannabis flower trimmings, wherein the cannabis flower trimmings contain trichomes;
   b. soaking and agitating the cannabis flower trimmings in the ice water for a sufficient time to allow at least some of the trichomes to separate from the cannabis flower trimmings;
   c. filtering the ice water mixture obtained in step b through a series of mesh screens of progressively smaller mesh and discarding the plant material that collects on the first mesh screen and removing the trichomes that collect on the remaining screens;
   d. placing the trichomes into a fine mesh sieve and pressing the trichomes through the fine mesh sieve onto a flat surface and spreading the trichomes as thinly as possible on the flat surface;
   e. drying and curing the trichomes in a cool, dry, dark environment for at least 2 weeks;
   f. grading and separating the trichomes into high- and low-purity sections, wherein the trichomes in the high-purity sections are ready for medical use;
   g. pulverizing or grinding up the high-purity trichomes and adding a sufficient amount of cream thereto to produce said topical ointment.
2. The method of claim 1, wherein
drying the trichomes includes heating the trichomes to at least 150 degrees Fahrenheit for at least 15 minutes.

* * * * *